(12) United States Patent
Menzl et al.

(10) Patent No.: US 9,204,231 B1
(45) Date of Patent: Dec. 1, 2015

(54) INDEPENDENT VOLUME CONTROL IN A BILATERAL AUDITORY PROSTHESIS SYSTEM

(71) Applicant: Advanced Bionics AG, Staefa (CH)

(72) Inventors: Stefan D. Menzl, Jona (CH); Hans-Uelii Roeck, Hombrechtikon (CH); Logan P. Palmer, Santa Monica, CA (US); Abhijit Kulkarni, Newbury Park, CA (US); Manish Vaishya, Valencia, CA (US); Volkmar Hamacher, Hannover (DE); Alexander Reich, North Hollywood, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/807,773

(22) Filed: Jul. 23, 2015

Related U.S. Application Data

(63) Continuation-in-part of application No. 14/729,016, filed on Jun. 2, 2015, which is a continuation of application No. 13/994,698, filed as application No. PCT/US2010/060754 on Dec. 16, 2010, now Pat. No. 9,061,149.

(51) Int. Cl.
*A61N 1/00* (2006.01)
*H04R 25/00* (2006.01)
(Continued)

(52) U.S. Cl.
CPC .......... *H04R 25/70* (2013.01); *A61N 1/36032* (2013.01); *A61N 1/37288* (2013.01)

(58) Field of Classification Search
CPC .................................................. A61M 5/14276
USPC ......................................... 607/3, 57; 381/312
See application file for complete search history.

(56) References Cited

U.S. PATENT DOCUMENTS

| 7,286,675 B1 | 10/2007 | O'Neill et al. |
| 2004/0208331 A1 | 10/2004 | Chalupper |

(Continued)

FOREIGN PATENT DOCUMENTS

WO  WO-2010/045358  4/2010

OTHER PUBLICATIONS

International Search Report and Written Opinion received in International Application No. PCT/US2010/60754 dated Feb. 16, 2011.
(Continued)

*Primary Examiner* — Theodore Stigwell
*Assistant Examiner* — Nadia A Mahmood
(74) *Attorney, Agent, or Firm* — ALG Intellectual Property, LLC

(57) ABSTRACT

An exemplary system includes 1) a first sound processor included in a first auditory prosthesis system associated with a first ear of a patient, the first sound processor including a first volume control facility, and 2) a second sound processor included in a second auditory prosthesis system associated with a second ear of the patient, the second sound processor including a second volume control facility. The first volume control facility adjusts, in response to actuation of the first volume control facility, a first volume level perceived by the patient when electrical stimulation is applied by either the first auditory prosthesis system or the second auditory prosthesis system. The second volume control facility adjusts, in response to actuation of the second volume control facility, a second volume level perceived by the patient when acoustic stimulation is applied by either the first auditory prosthesis system or the second auditory prosthesis system.

20 Claims, 12 Drawing Sheets

(51) Int. Cl.
    *A61N 1/36*    (2006.01)
    *A61N 1/372*   (2006.01)

(56) References Cited

U.S. PATENT DOCUMENTS

| | | |
|---|---|---|
| 2005/0129262 A1 | 6/2005 | Dillon et al. |
| 2005/0245991 A1 | 11/2005 | Faltys et al. |
| 2006/0287690 A1 | 12/2006 | Bouchataoui et al. |
| 2007/0076909 A1 | 4/2007 | Roeck et al. |
| 2007/0237346 A1 | 10/2007 | Fichtl et al. |
| 2010/0152813 A1 | 6/2010 | Lineaweaver et al. |
| 2010/0280307 A1 | 11/2010 | Lineaweaver et al. |

OTHER PUBLICATIONS

Non-Final Office Action received in U.S. Appl. No. 13/994,698 dated Mar. 10, 2014.
Extended European Search Report received in European Application No. 10860706.0, dated Jun. 26, 2014.
Communication pursuant to Rules 70(2) and 70a(2) EPC received in European Patent Application No. 10860706.0, dated Jul. 15, 2014.
Final Office Action received in U.S. Appl. No. 13/994,698 dated Nov. 6, 2014.

INDEPENDENT VOLUME CONTROL IN A BILATERAL AUDITORY PROSTHESIS SYSTEM

RELATED APPLICATIONS

The present application is a continuation-in-part application of U.S. application Ser. No. 14/729,016, filed Jun. 2, 2015, which application is a continuation application of U.S. application Ser. No. 13/994,698, filed Jun. 14, 2013 and issued as U.S. Pat. No. 9,061,149 on Jun. 23, 2015, which application is a U.S. National Stage Entry of PCT Application No. PCT/US10/60754, filed Dec. 16, 2010. The contents of these applications are incorporated herein by reference in their respective entireties.

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the cochlea are impeded. These sound pathways may be impeded, for example, by damage to the ossicular chain, excessive cerumen, or a malformed tympanic membrane. Mild conductive hearing losses can be treated with hearing aids, stronger losses may require a middle ear surgery or a bone-anchored hearing aid.

Sensorineural hearing loss, on the other hand, is primarily caused by the absence or destruction of the outer hair cells on the basilar membrane. There are rare cases in which sensorineural hearing loss is caused by a malfunction of the vestibulocochlear nerve or even the central processing system. To overcome sensorineural hearing loss, numerous cochlear implant systems—or cochlear prostheses—have been developed. Cochlear implant systems bypass the major part of the ear by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function. Cochlear implants are typically capable of providing high-frequency information up to 8 kHz.

There is a certain group of people that has some degree of residual hearing in the low frequencies (e.g., below 1 kHz) and a severe hearing loss in the high frequencies (e.g., above 1 kHz). These people cannot benefit from traditional amplification because of the severity of the hearing loss in the high frequencies. Nor are they classic cochlear implant candidates, because of their mostly intact low frequency residual hearing.

For this group of people, various electro-acoustic stimulation ("EAS") systems have been developed that provide such patients with the ability to perceive both low and high frequencies. Electro-acoustic stimulation refers to the use of a hearing aid and a cochlear implant together in the same ear. The hearing aid acoustically amplifies the low frequencies while the cochlear implant electrically stimulates the high frequencies. The auditory nerve combines the acoustic and electric stimuli to one auditory signal. Results of various studies have shown a highly synergistic effect between hearing aid and cochlear implant technology, particularly evident in speech understanding, pitch discrimination, and music appreciation.

However, electro-acoustic stimulation systems suffer from the problem that the perceptual sensitivity of a patient to acoustic stimulation is quite different than the perceptual sensitivity of the patient to electrical stimulation. For example, sensitivity of a patient to electrical stimulation often changes throughout the day and in accordance the health state of the patient while the sensitivity of the patient to acoustic stimulation is typically more consistent. Hence, it would be desirable for the patient to be able to independently adjust a volume associated with the acoustic stimulation and a volume associated with the electrical stimulation. Unfortunately, current electro-acoustic stimulation systems balance the two types of stimulation during the fitting process only and do to provide a control for the user to change the balance throughout the day.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
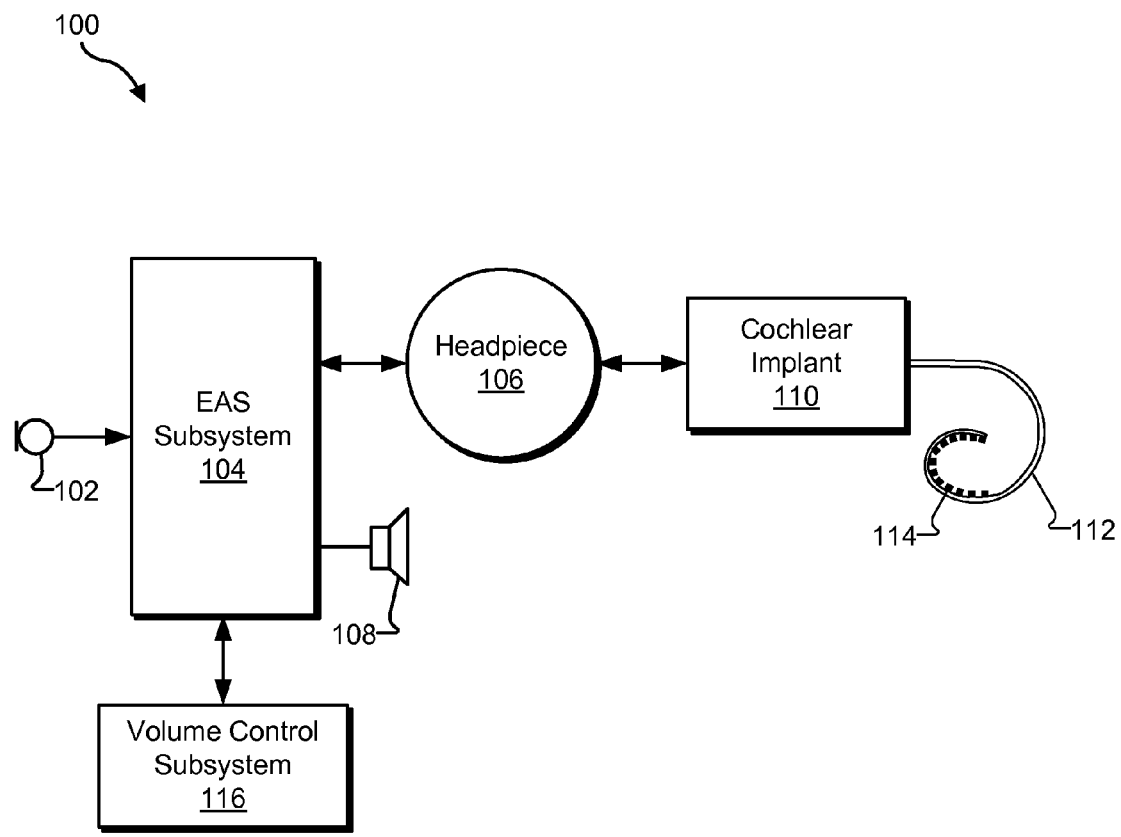
FIG. 1 illustrates an exemplary EAS system according to principles described herein.

Systems and methods for independent volume control in a bilateral auditory prosthesis system are described herein. As will be described below, a bilateral auditory prosthesis system may include a first auditory prosthesis system associated with a first ear of a patient and a second auditory prosthesis system associated with a second ear of the patient. The first auditory prosthesis system may include a first sound processor that includes a first volume control facility and the second auditory prosthesis system may include a second sound processor that includes a second volume control facility. Each volume control facility may be configured to control a different type of volume level for the entire bilateral auditory prosthesis system.

For example, the first volume control facility may be associated with electrical stimulation and the second volume control facility may be associated with acoustic stimulation. In this configuration, the first volume control facility adjusts, in response to actuation of the first volume control facility by a user, a first volume level perceived by the patient when electrical stimulation is applied by either the first auditory prosthesis system or the second auditory prosthesis system. Likewise, the second volume control facility adjusts, in response to actuation of the second volume control facility by the user, a second volume level perceived by the patient when acoustic stimulation is applied by either the first auditory prosthesis system or the second auditory prosthesis system.

Numerous advantages are associated with the systems and methods described herein. For example, the systems and methods described herein may allow a patient to selectively and independently control a volume associated with electrical stimulation provided by a bilateral auditory prosthesis system and a volume associated with acoustic stimulation provided by the bilateral auditory prosthesis system. This may be beneficial in many different scenarios. For example, some bilateral patients have to regularly adjust the electrical stimulation volume throughout the day due to a fading effect of the electrical stimulation. However, these patients may not desire to simultaneously adjust the acoustic stimulation volume, which is less affected by the fading effect. The systems and methods described herein may allow these patients to independently adjust the electrical stimulation volume without affecting the acoustic stimulation volume. Moreover, the systems and methods described herein may allow independent control of the electric and acoustic stimulation volume levels utilizing components (e.g., rotatable control dials) already included in (e.g., disposed on) sound processors.

Systems and methods for independent volume control in EAS systems are also described herein. In some examples, an EAS subsystem is configured to direct a cochlear implant to apply electrical stimulation representative of audio content included in a first frequency band (e.g., a "high" frequency band) to a patient. The EAS subsystem may be further configured to direct a receiver to apply acoustic stimulation representative of audio content included in a second frequency band (e.g., a "low" frequency band) to the patient. The frequency bands may be selected based on the hearing loss of the patient or a patient group. A volume control subsystem may be communicatively coupled to the EAS subsystem and configured to facilitate independent control of a volume associated with the electrical stimulation and a volume associated with the acoustic stimulation.

For example, the volume control subsystem may include a first volume control mechanism configured to adjust the volume associated with the electrical stimulation in response to actuation of the first volume control mechanism by a user and a second volume control mechanism configured to adjust the volume associated with the acoustic stimulation in response to actuation of the second volume control mechanism by the user. Additional or alternative implementations of the volume control subsystem will be described herein.

FIG. 1 illustrates an exemplary EAS system 100. EAS system 100 may include one or more microphones (e.g., microphone 102), an EAS subsystem 104, a headpiece 106, a receiver 108, a cochlear implant 110, and a lead 112 having a plurality of electrodes 114 disposed thereon. EAS system 100 may further include a volume control subsystem 116, which may be selectively and communicatively coupled to EAS subsystem 104. Each of the components shown in FIG. 1 may include or be implemented by any combination of hardware, software, and/or firmware as may serve a particular implementation. For example, volume control subsystem 116 may include or be implemented by a computing device or processor configured to perform one or more of the functions described herein. Each of the components shown in FIG. 1 will now be described in more detail.

Microphone 102 may detect an audio signal and input the audio signal (or an electrical signal representative of the audio signal) into EAS subsystem 104. Microphone 102 may include any type of microphone as may serve a particular implementation and may be located external to the patient, included within headpiece 106, positioned near or within the ear canal, and/or implanted within the patient as may serve a particular implementation.

EAS subsystem 104 may be configured to facilitate electro-acoustic stimulation of a patient. For example, EAS subsystem 104 may include any combination of components configured to direct cochlear implant 110 to apply electrical stimulation to the patient and to direct receiver 108 to apply acoustic stimulation to the patient. The electrical stimulation may be representative of audio content included in a "high" frequency band (e.g., a frequency band substantially equal to 1 kHz-8 kHz). The acoustic stimulation may be representative of audio content included in a "low frequency band (e.g., a frequency band substantially equal to 100 Hz to 1 kHz). It will be recognized that the frequency bands associated with both the electrical and acoustic stimulation may vary as may serve a particular implementation.

EAS subsystem 104 may be configured to operate in accordance with one or more control parameters. As used herein, a "control parameter" may include any parameter governing an operation of EAS subsystem 104. Exemplary control parameters include, but are not limited to, volume control parameters, microphone sensitivity parameters, program selection parameters, noise reduction parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters.

To illustrate, EAS subsystem 104 may process an audio signal (which may be detected by microphone 102, input by way of an auxiliary audio input port, etc.) in accordance with one or more control parameters (e.g., that may be associated with a particular sound processing strategy). EAS subsystem 104 may then direct cochlear implant 110 to generate and apply electrical stimulation representative of audio content included in the audio signal that is within the high frequency range at a volume level specified by a volume control parameter associated with the electrical stimulation. EAS subsystem 104 may additionally or alternatively direct receiver 108 to apply acoustic stimulation representative of audio content included in the audio signal that is within the low frequency range at a volume level specified by a volume control parameter associated with the acoustic stimulation.

EAS subsystem 104 may be implemented by any number of devices or components. For example, as will be described in more detail below, EAS subsystem 104 may be implemented by a single device that may be worn behind or on the ear, similar to conventional hearing aids and/or sound processors used in cochlear implant systems. Alternatively, EAS subsystem 104 may be implemented by a single device configured to be worn off the ear and/or implanted within the patient.

Headpiece 106 may be configured to be affixed to a patient's head and positioned such that a coil housed within headpiece is communicatively coupled to a corresponding coil included within cochlear implant 110. In this manner, control parameters and power signals may be wirelessly transmitted between EAS subsystem 104 and cochlear implant 110.

Receiver 108 may be positioned inside the ear canal of the patient (or at any other suitable location) and configured to apply acoustic stimulation to the patient. For example, receiver 108 may include a speaker configured to present an amplified version of audio content included in the low frequency band to the patient.

Cochlear implant 110, lead 112, and electrodes 114 may be partially or fully implanted within a patient and configured to apply electrical stimulation to one or more stimulation sites associated with an auditory pathway (e.g., the auditory nerve) of the patient. Cochlear implant 110 may include any type of implantable stimulator that may be used in association with the systems and methods described herein.

Volume control subsystem 116 may be selectively and communicatively coupled to EAS subsystem 104 and may be configured to facilitate independent control of a volume associated with the electrical stimulation provided by cochlear implant 110 and a volume associated with the acoustic stimulation provided by receiver 108.

Figure 2:
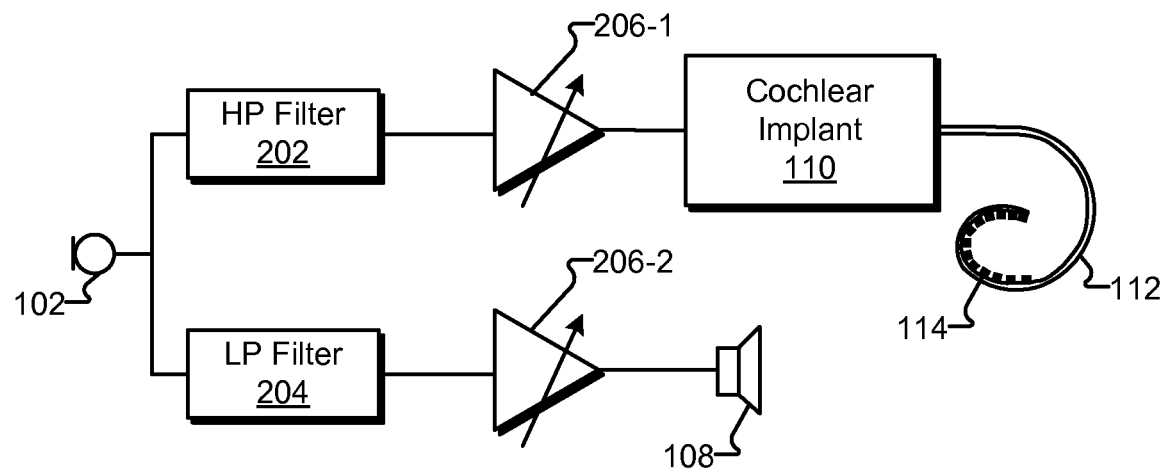
FIG. 2 shows a simplified diagram of exemplary components that may facilitate independent control of a volume associated with electrical stimulation provided by a cochlear implant and a volume associated with acoustic stimulation provided by a hearing aid receiver according to principles described herein.

To illustrate, FIG. 2 shows a simplified diagram of exemplary components that may implement volume control subsystem 116 by facilitating independent control of a volume associated with the electrical stimulation provided by cochlear implant 110 and a volume associated with the acoustic stimulation provided by receiver 108. As shown in FIG. 2, an audio signal detected by microphone 102 may be concurrently passed through a high pass filter 202 and a low pass filter 204. It will be recognized that in some implementations, high pass filter 202 and/or low pass filter 204 may include band pass filters. High pass filter 202 may include any suitable combination of analog and/or digital components configured to remove low frequency audio content (e.g., less than about 1 kHz) and pass the remaining high frequency audio content to variable amplifier 206-1. Variable amplifier 206-1 may be configured to adjust a volume, or gain, of the high frequency audio content. For example, variable amplifier 206-1 may direct cochlear implant 110 to adjust an amplitude of the electrical stimulation that is applied to the patient to represent the high frequency audio content.

Likewise, low pass filter 204 may include any suitable combination of analog and/or digital components configured to remove high frequency audio content (e.g., greater or equal to about 1 kHz) and pass the remaining low frequency audio content to variable amplifier 206-2. Variable amplifier 206-2 may be configured to adjust a volume, or gain, of the low frequency audio content. For example, variable amplifier 206-2 may adjust an amplitude of the acoustic stimulation that is applied to the patient by way of receiver 108 to represent the low frequency audio content.

In some examples, variable amplifiers 206-1 and 206-2 may be configured to adjust the volumes associated with the electrical and acoustic stimuli, respectively, in response to user input provided by the patient and/or another user. Exemplary user input may include, as will be described in more detail below, user actuation of one or more volume control mechanisms.

Figure 3:
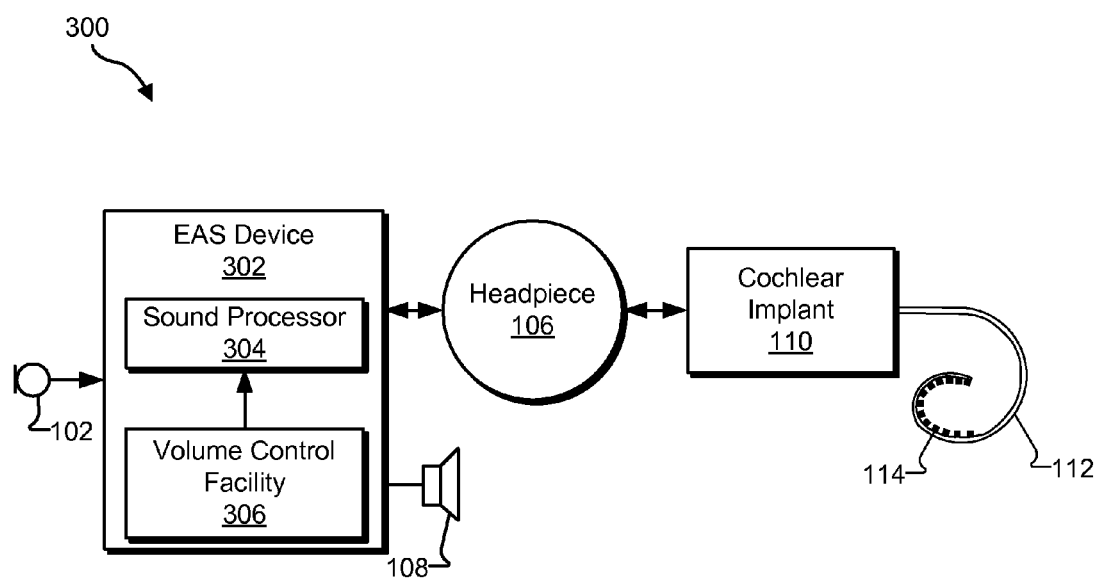
FIG. 3 shows an exemplary implementation of the EAS system of FIG. 1 according to principles described herein.

Returning to FIG. 1, EAS subsystem 104 and volume control subsystem 116 may be implemented by any combination of components as may serve a particular implementation. For example, EAS subsystem 104 and volume control subsystem 116 may be implemented by a single device. To illustrate, FIG. 3 shows an exemplary implementation 300 of EAS system 100 in which a single EAS device 302 is configured to implement EAS subsystem 104 and volume control subsystem 116. EAS device 302 may be dimensioned to fit behind or on the ear of a patient. Alternatively, EAS device 302 may be worn or carried off the ear by the patient.

As shown in FIG. 3, EAS device 302 may include a sound processor 304 and a volume control facility 306 communicatively coupled one to another. Sound processor 304 may include any combination of components configured to process an audio signal and direct cochlear implant 110 to apply electrical stimulation representative of high frequency content included in the audio signal to the patient and to direct receiver 108 to apply acoustic stimulation representative of low frequency content included in the audio signal to the patient.

Volume control facility 306 may include any combination of components configured to facilitate independent control of a volume associated with the electrical stimulation provided by cochlear implant 110 and a volume associated with the acoustic stimulation provided by receiver 108. For example, volume control facility 306 may include separate volume control mechanisms associated with each of the electrical stimulation and the acoustic stimulation, respectively.

Figure 4:
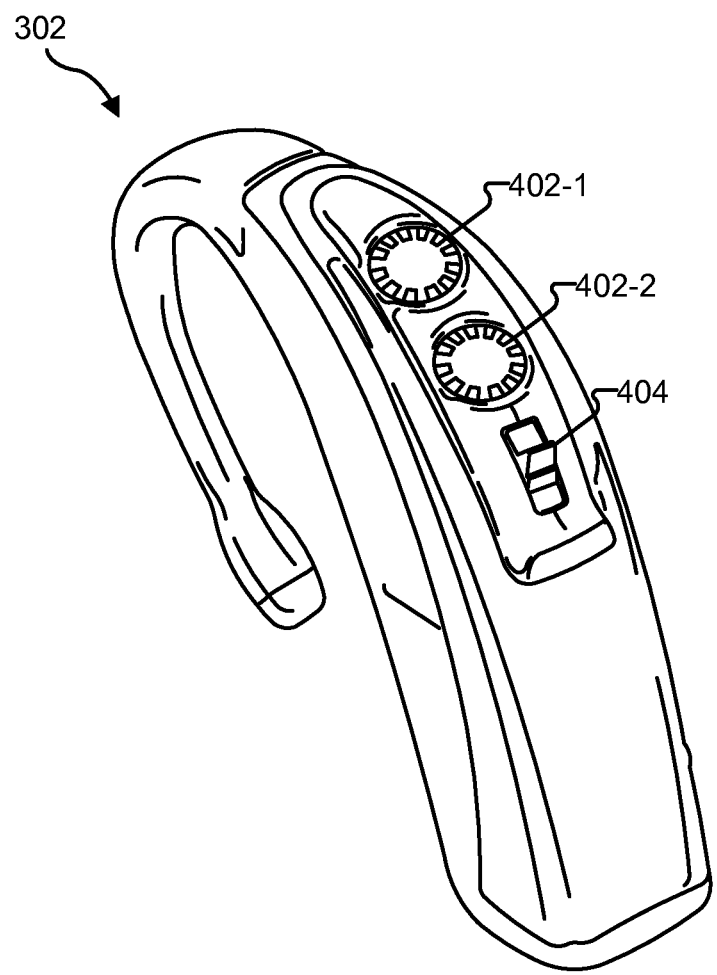
FIGS. 4-6 shows perspective views of exemplary EAS devices according to principles described herein.

To illustrate, FIG. 4 shows a perspective view of an exemplary EAS device 302 that includes a first volume control mechanism 402-1 and a second volume control mechanism 402-2 (collectively referred to herein as "volume control mechanisms 402") disposed on an outer surface of EAS device 302. Volume control mechanisms 402 may include rotatable control dials, as shown in FIG. 4, or any other type of control mechanism that may be actuated by a user.

First volume control mechanism 402-1 may be configured to adjust the volume associated with the electrical stimulation provided by cochlear implant 110 in response to actuation of first volume control mechanism 402-1 by a user and second volume control mechanism 402-2 may be configured to adjust the volume associated with the acoustic stimulation provided by receiver 108 in response to actuation of second volume control mechanism 402-2 by the user. Hence, the user may increase or decrease the volume associated with the electrical stimulation provided by cochlear implant 110 by actuating (e.g., rotating clockwise or counter-clockwise) first volume control mechanism 402-1. Likewise, the user may increase or decrease the volume associated with the acoustic stimulation provided by receiver 108 by actuating (e.g., rotating clockwise or counter-clockwise) second volume control mechanism 402-2.

FIG. 4 also shows that EAS device 302 may include a program selection switch 404 configured to facilitate selection by a user of one or more programs (i.e., sound processing strategies) by which EAS device 302 may operate. To illustrate, program selection switch 404 may be selectively positioned in one of two positions. Each position corresponds to a particular program. For example, the first position may correspond to a "normal" program wherein EAS device 302 may operate in accordance with one or more default control parameters. The second position may correspond to a "noise reduction" program, wherein EAS device 302 may operate in accordance with one or more noise reduction parameters. In some examples, the volume associated with the electrical stimulation provided by cochlear implant 110 and the volume associated with the acoustic stimulation provided by receiver 108 may be automatically adjusted in accordance with a positioning of program selection switch 404.

In some alternative embodiments, first volume control mechanism 402-1 may serve as an overall volume control mechanism configured to adjust an overall volume associated with both the electrical stimulation and the acoustic stimulation in response to actuation of first volume control mechanism 402-1 by a user. Second volume control mechanism 402-2 may serve as a balance control mechanism configured to adjust the volume associated with the electrical stimulation relative to the volume associated with the acoustic stimulation in response to actuation of second volume control mechanism 402-2 by the user. For example, the user may rotate second volume control mechanism 402-2 in a clockwise direction to increase the volume associated with the electrical stimulation relative to the volume associated with the acoustic stimulation. Likewise, the user may rotate second volume control mechanism 402-2 in a counter-clockwise direction to decrease the volume associated with the electrical stimulation relative to the volume associated with the acoustic stimulation.

Figure 5:
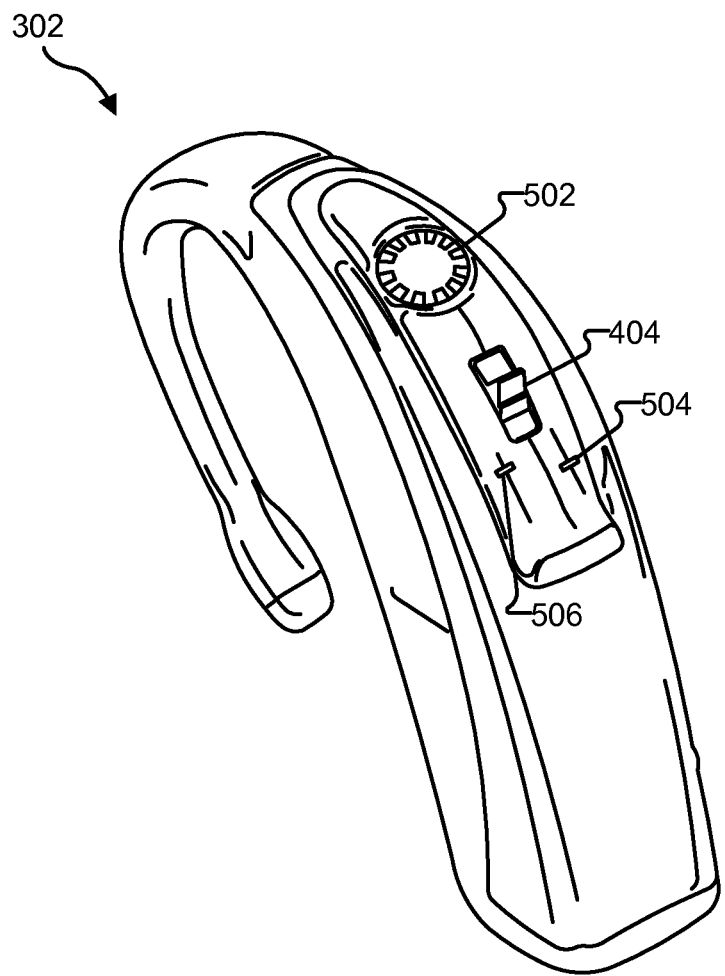

FIG. 5 illustrates an alternative implementation of volume control facility 306. As shown in FIG. 5, EAS device 302 may alternatively include an overall volume control mechanism 502, a treble control mechanism 504, and a bass control mechanism 506 disposed on an outer surface of EAS device 302. Overall volume control mechanism 502 may include a rotatable control dial or the like and may be configured to adjust an overall volume associated with both the electrical stimulation and the acoustic stimulation in response to actuation of overall volume control mechanism 502 by a user. Treble control mechanism 504 and bass control mechanism 506 may include slideable levers, as shown in FIG. 5, or any other suitable type of mechanism and may facilitate tone balance control. For example, the user may actuate treble control mechanism 504 to fine tune or otherwise adjust the volume associated with the electrical stimulation provided by cochlear implant 110. Additionally or alternatively, the user may actuate bass control mechanism 506 to fine tune or otherwise adjust the volume associated with the acoustic stimulation provided by receiver 108.

Figure 6:
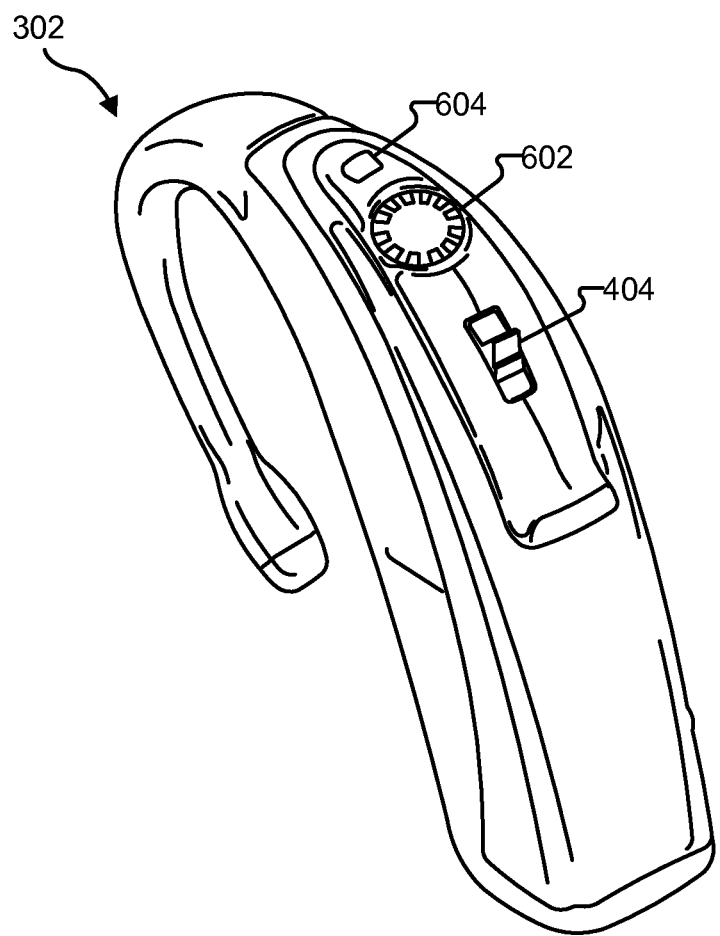

FIG. 6 illustrates another alternative implementation of volume control facility 306. As shown in FIG. 6, EAS device 302 may alternatively include a single volume control mechanism 602 and a selection mechanism 604 communicatively coupled to volume control mechanism 602. Selection mechanism 604 may include a button, switch, or any other type of selection mechanism and may be used by a user to selectively associate volume control mechanism 602 with either the electrical stimulation provided by cochlear implant 110 or the acoustic stimulation provided by receiver 108.

For example, a user may actuate (e.g., press) selection mechanism 604 to selectively associate volume control mechanism 602 with the electrical stimulation provided by cochlear implant 110. The user may then actuate (e.g., rotate) volume control mechanism 602 to adjust the volume associated with the electrical stimulation provided by cochlear implant 110. The user may subsequently actuate (e.g., press) selection mechanism 604 again to selectively associate volume control mechanism 602 with the acoustic stimulation provided by receiver 108. The user may then actuate (e.g., rotate) volume control mechanism 602 to adjust the volume associated with the acoustic stimulation provided by receiver 108. In this or a similar manner, the electrical stimulation volume and the acoustic stimulation volume may be independently controlled using a single volume control mechanism.

Additionally or alternatively, volume control facility 306 may include a sensor communicatively coupled to volume control mechanism 602. The sensor may be configured to detect a volume control factor and automatically associate volume control mechanism 602 with either the electrical stimulation provided by cochlear implant 110 or the acoustic stimulation provided by receiver 108 based on the detected volume control factor. The volume control factor may include any factor associated with EAS device 302 as may serve a particular implementation. For example, the volume control factor may include a time of day, an acoustic environment of the patient, and/or any other suitable factor.

To illustrate, the user may typically adjust the volume associated with acoustic stimulation provided by receiver 108 in the morning immediately after waking up and the volume associated with the electrical stimulation provided by cochlear implant 110 throughout the day. Sensor may therefore detect the time of day and cause volume control mechanism 602 to be associated with the acoustic stimulation provided by receiver 108 during a predetermined time period in the morning and with the electrical stimulation provided by cochlear implant 110 during the remainder of the day. In this manner, the user does not have to manually associate volume control mechanism 602 with the desired type of stimulation each time he or she desires to adjust one of the volume levels.

To further illustrate, volume control mechanism 602 may be automatically associated with either the electrical stimulation provided by cochlear implant 110 or the acoustic stimulation provided by receiver 108 based on a detected acoustic environment of the patient. For example, the sensor may detect that the patient has entered an environment where it is desirable for the user to hear speech. Sensor may accordingly cause volume control mechanism 602 to be associated with electrical stimulation provided by cochlear implant 110 so that the patient may increase the volume associated with the electrical stimulation as desired in order to better perceive the speech.

In some alternative embodiments, selection mechanism 604 may be used by a user to selectively associate volume control mechanism 602 with an overall volume level associated with both the electrical stimulation and the acoustic stimulation or with a balance between a volume level associated with the electrical stimulation and a volume level associated with the acoustic stimulation. For example, a user may actuate (e.g., press) selection mechanism 604 to selectively associate volume control mechanism 602 with an overall volume associated with both the electrical stimulation and the acoustic stimulation. The user may then actuate (e.g., rotate) volume control mechanism 602 to adjust the overall volume level. The user may subsequently actuate (e.g., press) selection mechanism 604 again to selectively associate volume control mechanism 602 with a balance between the electrical and acoustic stimulation volumes. The user may then actuate (e.g., rotate) volume control mechanism 602 to adjust the volume associated with the electrical stimulation relative to the volume associated with the acoustic stimulation. For example, rotating volume control mechanism 602 in a clockwise direction may simultaneously increase the electrical stimulation volume and decrease the acoustic stimulation volume. Rotating volume control mechanism 602 in a counter-clockwise may simultaneously decrease the electrical stimulation volume and increase the acoustic stimulation volume.

In some alternative embodiments, volume control mechanism 602 may include an intelligent volume control mechanism configured to be selectively associated with the electrical stimulation or the acoustic stimulation in accordance with one or more features extracted from an audio signal. For example, the signal energy in the low and high frequency bands may be detected and used to selectively associated volume control mechanism 602 with the electrical stimulation or the acoustic stimulation. In this manner, volume control mechanism 602 may change the volume where it makes most sense.

Figure 7:
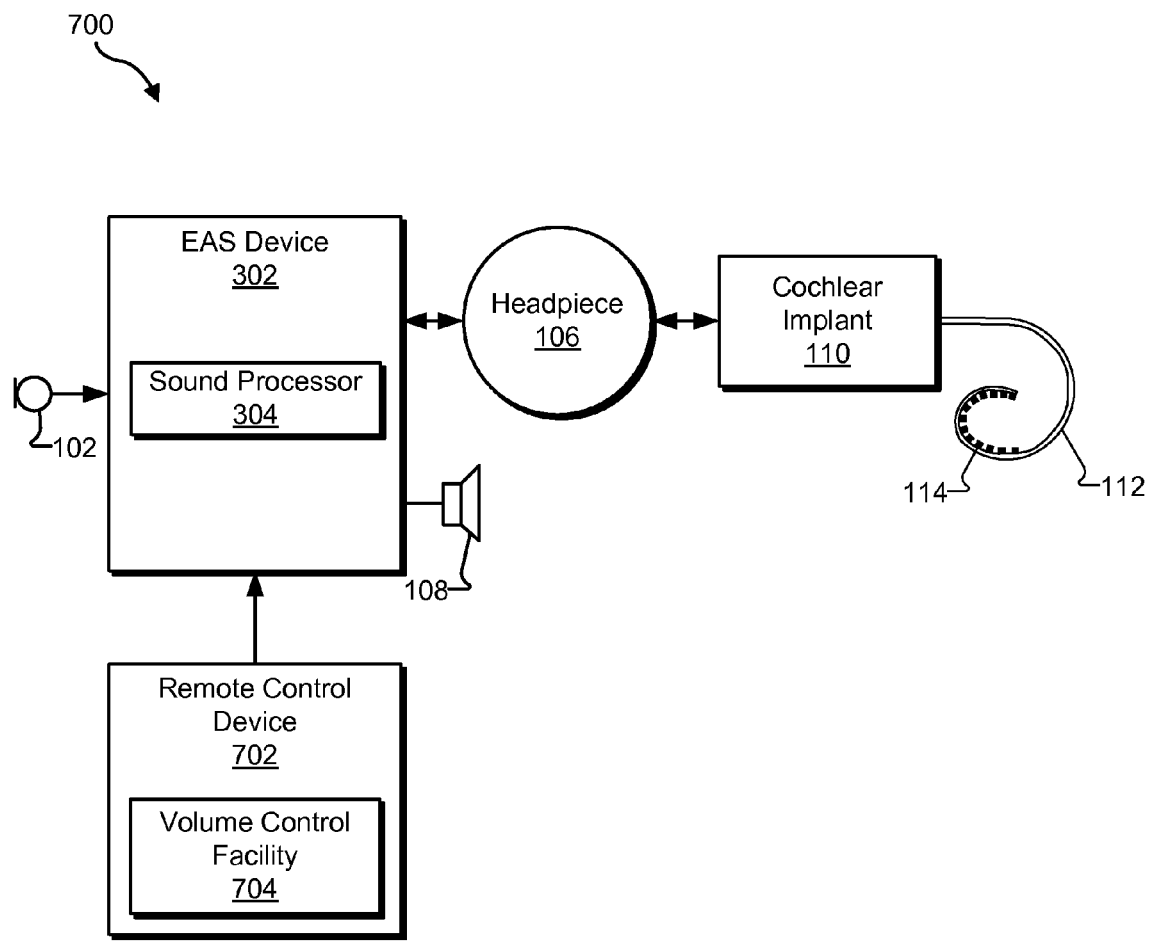
FIG. 7 shows another exemplary implementation of the EAS system of FIG. 1 according to principles described herein.

Returning to FIG. 1, EAS subsystem 104 and volume control subsystem 116 may alternatively be implemented by separate devices. To illustrate, FIG. 7 shows an exemplary implementation 700 of EAS system 100 in which EAS device 302 is configured to implement EAS subsystem 104 and remote control device 702 is configured to implement volume control subsystem 116. Remote control device 702 may include any type of computing device selectively and communicatively coupled to EAS device 302 and may include a volume control facility 704, which may be similar to volume control facility 306. For example, volume control facility 704 may include one or more volume control mechanisms similar to those described herein that are configured to facilitate independent control of the volume associated with the electrical stimulation provided by cochlear implant 110 and the volume associated with the acoustic stimulation provided by receiver 108.

Volume control subsystem 116 may be configured to perform one or more operations in addition to facilitating independent control of the volume associated with the electrical stimulation provided by cochlear implant 110 and the volume associated with the acoustic stimulation provided by receiver 108. Examples of such operations will now be provided.

In some examples, volume control subsystem 116 may be configured to log one or more adjustments to the volume associated with the electrical stimulation and with the volume associated with the acoustic stimulation during a specified time period. For example, volume control subsystem 116 may be configured to store data representative of the adjustments in a storage device that may be a part of or otherwise associated with EAS device 302, remote control device 702, and/or any other device. Based on the logged one or more adjustments, volume control subsystem 116 may calculate an average volume level associated with the electrical stimulation and an average volume level associated with the acoustic stimulation. Volume control subsystem 116 may then detect a predetermined event associated with EAS subsystem 104 and automatically set, in response to the predetermined event, the electrical stimulation volume to the calculated average electrical stimulation volume level and the acoustic stimulation volume to the calculated average acoustic stimulation volume level.

For example, volume control subsystem 116 may detect a rebooting of EAS device 302. In response, volume control subsystem 116 may automatically set the electrical stimulation volume to the calculated average electrical stimulation volume level and the acoustic stimulation volume to the calculated average acoustic stimulation volume level. In this manner, the user may only have to make minimal adjustments to the respective volumes levels in order to achieve desired volume levels after EAS device 302 reboots.

Additionally or alternatively, volume control subsystem 116 may be configured to automatically adjust at least one of the volume associated with the electrical stimulation provided by cochlear implant 110 and the volume associated with the acoustic stimulation provided by receiver 108 to result in substantially consistent timbre perception for broadband input signals of different amplitudes. This may be performed during a fitting process, for example, and may result in an optimized listening experience for the patient.

In some examples, a patient may be fitted with a bilateral auditory prosthesis system. For example, the patient may have a distinct cochlear implant and a distinct receiver for each ear. Volume control subsystem 116 may be configured to facilitate independent control of the electrical and acoustic stimulation volumes for each ear. Alternatively, any adjustments made to a volume level associated with the electrical or acoustic stimulation corresponding to one ear may be automatically applied to the electrical or acoustic stimulation associated with the other ear. Volume control subsystem 116 may be implemented by one or more volume control mechanisms on one side or both sides of the bilateral auditory prosthesis system. To illustrate, an electrical stimulation volume control mechanism may be located on the left side while an acoustic stimulation volume control mechanism may be located on the right side (or vice versa). Alternatively, an overall volume control mechanism may be located on the left side while a balance control mechanism may be located on the right side (or vice versa). Alternatively, all of the volume control mechanisms may be located on a single side (e.g., the left side).

Figure 8:
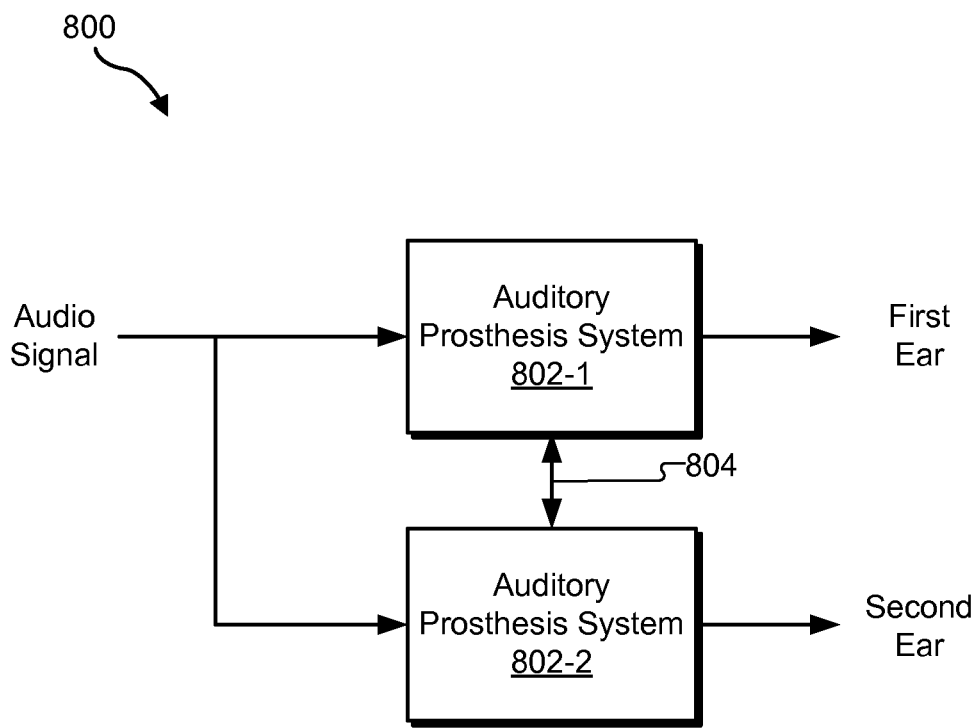
FIGS. 8-11 show various bilateral auditory prosthesis system configurations according to principles described herein.

FIG. 8 shows an exemplary bilateral auditory prosthesis system 800 that may be fitted to a patient. As shown, bilateral auditory prosthesis system 800 includes a first auditory prosthesis system 802-1 associated with a first ear of the patient and a second auditory prosthesis system 802-2 associated with a second ear of the patient. Each auditory prosthesis system 802-1 and 802-2 may detect an audio signal and provide electrical and/or acoustic stimulation representative of the audio signal to its respective ear. As shown, auditory prosthesis systems 802-1 and 802-2 may communicate one with another by way of a communication link 804 that interconnects auditory prosthesis systems 802-1 and 802-2. Communication link 804 may include any suitable wired and/or wireless link as may serve a particular implementation.

Auditory prosthesis systems 802-1 and 802-2 may each be implemented by any suitable type of auditory prosthesis system. For example, auditory prosthesis systems 802-1 and 802-2 may each be implemented by an EAS system configured to apply both electrical and acoustic stimulation to an ear of the patient, a cochlear implant system configured to apply only electrical stimulation to an ear of the patient, or a hearing aid configured to apply only acoustic stimulation to the patient. Various bilateral auditory prosthesis system configurations will now be described in connection with FIGS. 9-11.

Figure 9:
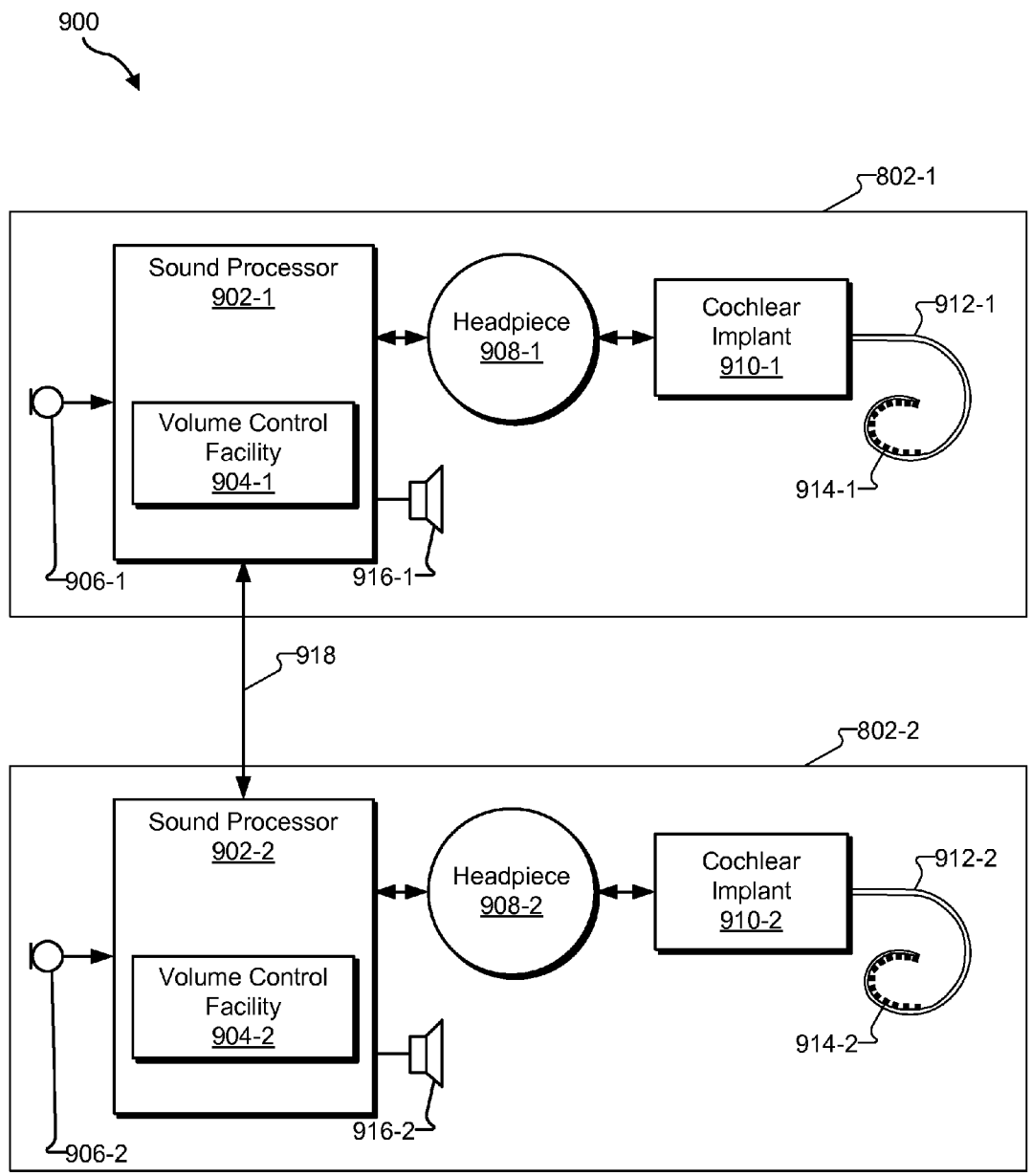

FIG. 9 illustrates an exemplary configuration 900 in which first and second auditory prosthesis systems 802-1 and 802-2 are both implemented by an EAS system. For example, as shown in FIG. 9, first auditory prosthesis system 802-1 includes a sound processor 902-1 that includes a volume control facility 904-1, a microphone 906-1, a headpiece 908-1, a cochlear implant 910-1, a lead 912-1 having a plurality of electrodes 914-1 disposed thereon, and a receiver 916-1. Likewise, second auditory prosthesis system 802-2 includes a sound processor 902-2 that includes a volume control facility 904-2, a microphone 906-2, a headpiece 908-2, a cochlear implant 910-2, a lead 912-2 having a plurality of electrodes 914-2 disposed thereon, and a receiver 916-2.

Volume control facilities 904-1 and 904-2 may each be implemented in any of the ways described herein. For example, volume control facility 904-1 may be implemented by a rotatable control dial disposed on a surface of sound processor 902-1 and volume control facility 904-2 may be implemented by a rotatable control dial disposed on a surface of sound processor 902-2.

To facilitate independent volume control, volume control facility 904-1 may be associated with electrical stimulation and volume control facility 904-2 may be associated with acoustic stimulation. Each volume control facility 904-1 and 904-2 may be selectively associated with its respective type of stimulation in any of the ways described herein. In this configuration, volume control facility 904-1 adjusts, in response to actuation of volume control facility 904-1 by a user (e.g., the patient or a person other than the patient), a first volume level perceived by the patient when electrical stimulation is applied by either the first auditory prosthesis system 802-1 or the second auditory prosthesis system 802-2. Likewise, volume control facility 904-2 adjusts, in response to actuation of volume control facility 904-2 by the user, a second volume level perceived by the patient when acoustic stimulation is applied by either the first auditory prosthesis system 802-1 or the second auditory prosthesis system 802-2. In this manner, the electrical and acoustic stimulation volumes for both auditory prosthesis systems 802-1 and 802-2 may be independently controlled without the need for a separate remote control.

As shown in FIG. 9, sound processors 902-1 and 902-2 may communicate with each other by way of communication link 804. For example, actuation of volume control facility 904-1 may set the first volume level to a particular value. In response, sound processor 902-1 may transmit data representative of the particular value to sound processor 902-2 by way of communication link 804. In this manner, sound processor 902-2 may adjust the volume level of electrical stimulation applied by auditory prosthesis system 802-2 based on the actuation of volume control facility 904-1. Likewise, actuation of volume control facility 904-2 may set the second volume level to a particular value. In response, sound processor 902-2 may transmit data representative of the particular value to sound processor 902-1 by way of communication link 804. In this manner, sound processor 902-1 may adjust the volume level of acoustic stimulation applied by auditory prosthesis system 802-1 based on the actuation of volume control facility 904-2.

Figure 10:
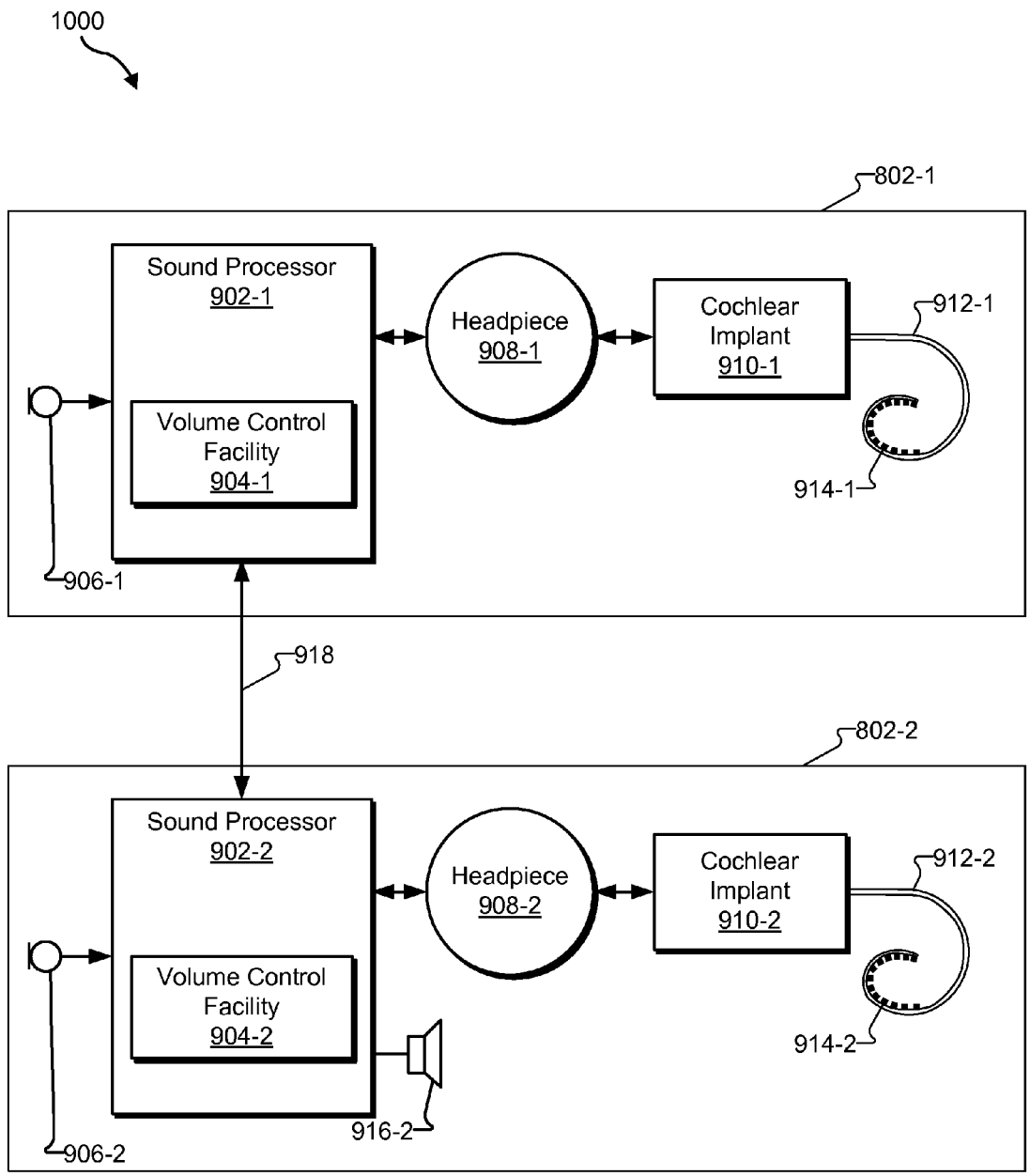

FIG. 10 illustrates an exemplary configuration 1000 in which first auditory prosthesis system 802-1 is implemented by a cochlear implant system and second auditory prosthesis system 802-2 is implemented by an EAS system. As shown, configuration 1000 is similar to configuration 900, except that in configuration 1000, first auditory prosthesis system 802-1 is configured to apply only electrical stimulation to the first ear of the patient. As described above, actuation of volume control facility 904-1 shown in FIG. 10 may adjust the volume level of electrical stimulation applied by either first auditory prosthesis system 802-1 or second auditory prosthesis system 802-2. However, actuation of volume control facility 904-2 shown in FIG. 10 adjusts the volume level of acoustic stimulation applied by second auditory prosthesis system 802-2 only. This is because first auditory prosthesis system 802-1 is not configured to provide acoustic stimulation in configuration 1000.

Figure 11:
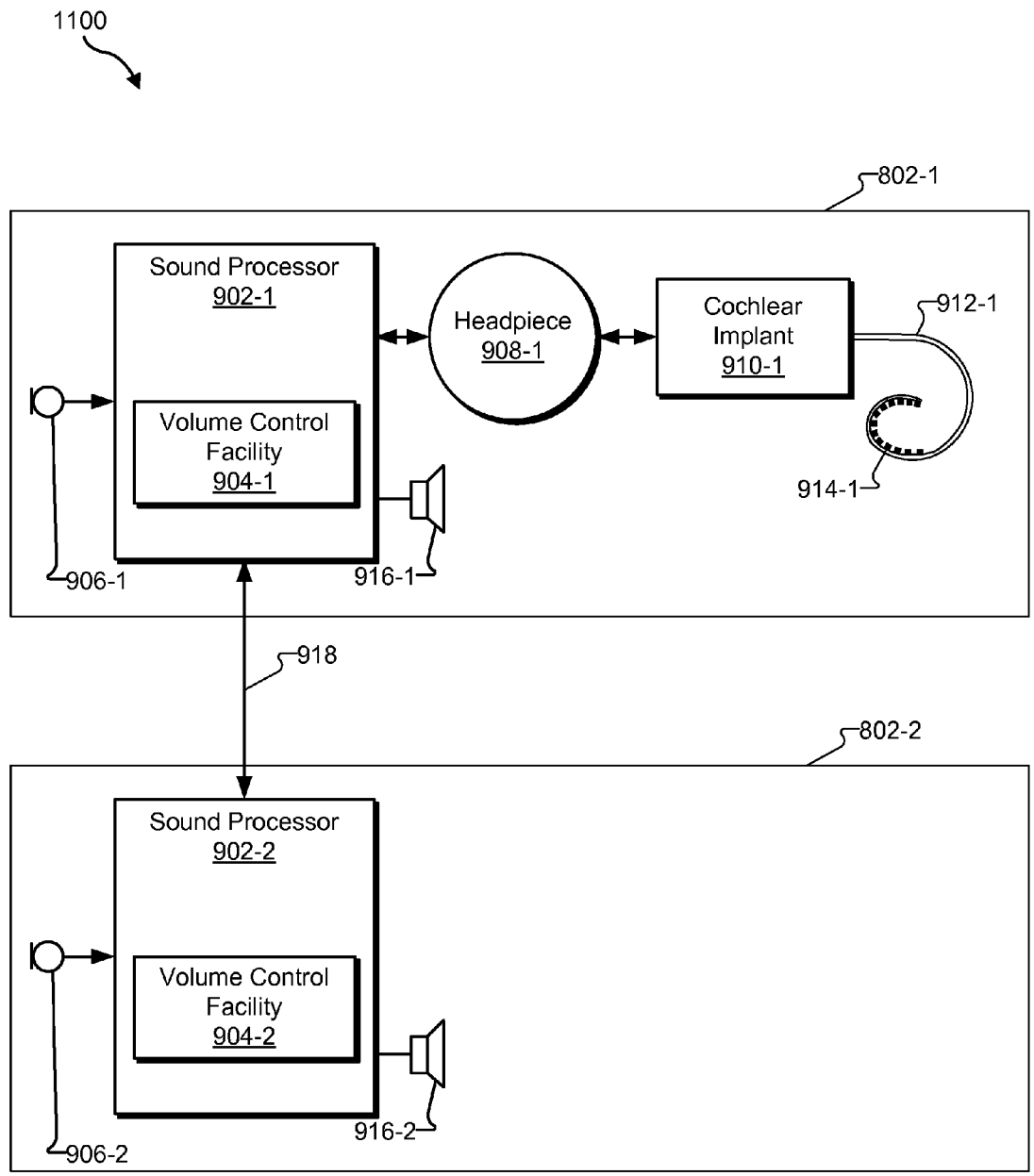

FIG. 11 illustrates an exemplary configuration 1100 in which first auditory prosthesis system 802-1 is implemented by an EAS system and second auditory prosthesis system 802-2 is implemented by a hearing aid. As shown, configuration 1100 is similar to configuration 900, except that in configuration 1100, second auditory prosthesis system 802-2 is configured to apply only acoustic stimulation to the second ear of the patient. As described above, actuation of volume control facility 904-2 shown in FIG. 11 may adjust the volume level of acoustic stimulation applied by either first auditory prosthesis system 802-1 or second auditory prosthesis system 802-2. However, actuation of volume control facility 904-2 shown in FIG. 11 adjusts the volume level of electrical stimulation applied by first auditory prosthesis system 802-1 only. This is because second auditory prosthesis system 802-2 is not configured to provide electrical stimulation in configuration 1100.

Returning to FIG. 9, in some alternative configurations, volume control facility 904-1 is configured to adjust, in response to actuation of volume control facility 904-1, an overall volume level perceived by the patient when electrical stimulation or acoustic stimulation is applied by either the first auditory prosthesis system 802-1 or the second auditory prosthesis system 802-2. In these configurations, volume control facility 904-2 is configured to adjust, in response to actuation of volume control facility 904-2, a balance between 1) a first volume level perceived by the patient when electrical stimulation is applied by either the first auditory prosthesis system 802-1 or the second auditory prosthesis system 802-2, and 2) a second volume level perceived by the patient when acoustic stimulation is applied by either the first auditory prosthesis system 802-1 or the second auditory prosthesis system 802-2.

Adjustment of the overall volume level and the balance may be facilitated by communication link 918. For example, actuation of volume control facility 904-1 may set the overall volume level to a particular value. In response, sound processor 902-1 may transmit data representative of the particular value to sound processor 902-2 by way of communication link 918. Sound processor 902-2 may adjust the overall volume level in accordance with transmitted data.

Likewise, actuation of volume control facility 904-2 may set the balance to a particular value. In response, sound processor 902-2 may transmit data representative of the particular value to sound processor 902-1 by way of communication link 918. Sound processor 902-1 may adjust the balance in accordance with transmitted data.

Figure 12:
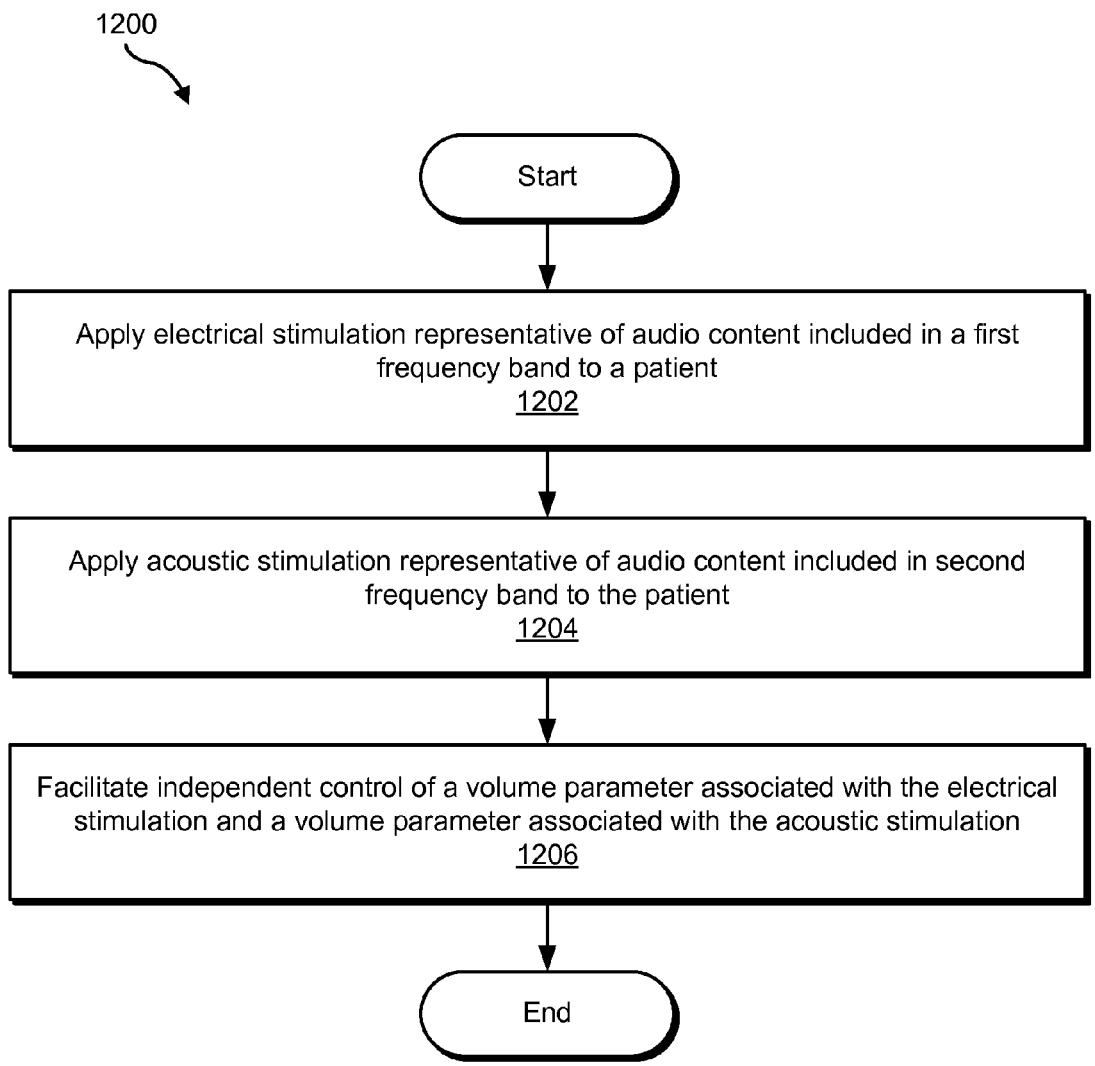
FIG. 12 illustrates an exemplary method of facilitating independent volume control in an EAS system according to principles described herein.

FIG. 12 illustrates an exemplary method 1200 of facilitating independent volume control in an EAS system. While FIG. 12 illustrates exemplary steps according to one embodiment, other embodiments may omit, add to, reorder, and/or modify any of the steps shown in FIG. 12. One or more of the steps shown in FIG. 12 may be performed by any component or combination of components of EAS subsystem 104, volume control subsystem 116, EAS device 116, and/or remote control device 702.

In step 1202, electrical stimulation representative of audio content included in a first frequency band is applied to a patient. Step 1202 may be performed in any of the ways described herein.

In step 1204, acoustic stimulation representative of audio content included in second frequency band is applied to the patient. Step 1204 may be performed in any of the ways described herein.

In step 1206, independent control of a volume parameter associated with the electrical stimulation and a volume parameter associated with the acoustic stimulation is facilitated. Step 1206 may be performed in any of the ways described herein.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a first sound processor included in a first auditory prosthesis system associated with a first ear of a patient, the first sound processor including a first volume control facility; and
a second sound processor included in a second auditory prosthesis system associated with a second ear of the patient, the second sound processor including a second volume control facility;
wherein
the first volume control facility adjusts, in response to actuation of the first volume control facility by a user, a first volume level perceived by the patient when electrical stimulation is applied by either the first auditory prosthesis system or the second auditory prosthesis system, and
the second volume control facility adjusts, in response to actuation of the second volume control facility by the user, a second volume level perceived by the patient when acoustic stimulation is applied by either the first auditory prosthesis system or the second auditory prosthesis system.

2. The system of claim 1, wherein:
the actuation of the first volume control facility sets the first volume level to a particular value; and
the first sound processor transmits data representative of the particular value to the second sound processor by way of a communication link that interconnects the first and second sound processors.

3. The system of claim 2, wherein the communication link comprises a wireless link.

4. The system of claim 1, wherein:
the actuation of the second volume control facility sets the second volume level to a particular value; and
the second sound processor transmits data representative of the particular value to the first sound processor by way of a communication link that interconnects the first and second sound processors.

5. The system of claim 4, wherein the communication link comprises a wireless link.

6. The system of claim 1, wherein:
the first auditory prosthesis system comprises a first electro-acoustic system configured to apply both electrical stimulation and acoustic stimulation to the first ear of the patient; and
the second auditory prosthesis system comprises a second electro-acoustic system configured to apply both electrical stimulation and acoustic stimulation to the second ear of the patient.

7. The system of claim 1, wherein:
the first auditory prosthesis system comprises a cochlear implant system configured to apply only electrical stimulation to the first ear of the patient; and
the second auditory prosthesis system comprises an electro-acoustic system configured to apply both electrical stimulation and acoustic stimulation to the second ear of the patient.

8. The system of claim 1, wherein:
the first auditory prosthesis system comprises an electro-acoustic system configured to apply both electrical stimulation and acoustic stimulation to the first ear of the patient; and
the second auditory prosthesis system comprises a hearing aid configured to apply only acoustic stimulation to the second ear of the patient.

9. The system of claim 1, wherein:
the first volume control facility is disposed on a surface of the first sound processor; and
the second volume control facility is disposed on a surface of the second sound processor.

10. The system of claim 1, wherein at least one of the first and second volume control facilities comprises a rotatable control dial.

11. The system of claim 1, wherein the user is the patient.

12. The system of claim 1, wherein the user is a person other than the patient.

13. A system comprising:
a first sound processor included in a first auditory prosthesis system associated with a first ear of a patient, the first sound processor including a first volume control facility; and
a second sound processor included in a second auditory prosthesis system associated with a second ear of the patient, the second sound processor including a second volume control facility;
wherein
the first volume control facility adjusts, in response to actuation of the first volume control facility by a user, an overall volume level perceived by the patient when electrical stimulation or acoustic stimulation is applied by either the first auditory prosthesis system or the second auditory prosthesis system, and
the second volume control facility adjusts, in response to actuation of the second volume control facility by the user, a balance between
a first volume level perceived by the patient when the electrical stimulation is applied by either the first auditory prosthesis system or the second auditory prosthesis system, and
a second volume level perceived by the patient when the acoustic stimulation is applied by either the first auditory prosthesis system or the second auditory prosthesis system.

14. The system of claim 13, wherein:
the actuation of the first volume control facility sets the overall volume level to a particular value; and
the first sound processor transmits data representative of the particular value to the second sound processor by way of a communication link that interconnects the first and second sound processors.

15. The system of claim 13, wherein:
the actuation of the second volume control facility sets the balance to a particular value; and
the second sound processor transmits data representative of the particular value to the first sound processor by way of a communication link that interconnects the first and second sound processors.

16. The system of claim 13, wherein:
the first auditory prosthesis system comprises a first electro-acoustic system configured to apply both electrical stimulation and acoustic stimulation to the first ear of the patient; and
the second auditory prosthesis system comprises a second electro-acoustic system configured to apply both electrical stimulation and acoustic stimulation to the second ear of the patient.

17. The system of claim 13, wherein:
the first volume control facility is disposed on a surface of the first sound processor; and
the second volume control facility is disposed on a surface of the second sound processor.

18. The system of claim 13, wherein at least one of the first and second volume control facilities comprises a rotatable control dial.

19. The system of claim 13, wherein the user is the patient.

20. The system of claim 13, wherein the user is a person other than the patient.

* * * * *